US00PP23958P2

(12) United States Plant Patent
Hutchins

(10) Patent No.: US PP23,958 P2
(45) Date of Patent: Oct. 8, 2013

(54) ***ALYOGYNE* PLANT NAMED 'HUTWOW'**

(50) Latin Name: *Alyogyne huegelii×hakeifolia*
Varietal Denomination: HUTWOW

(76) Inventor: Graham Hutchins, Hornchurch (GB)

( * ) Notice: Subject to any disclaimer, the term of this patent is extended or adjusted under 35 U.S.C. 154(b) by 273 days.

(21) Appl. No.: 13/135,211

(22) Filed: Jun. 29, 2011

(51) Int. Cl.
*A01H 5/00* (2006.01)

(52) U.S. Cl.
USPC ..... Plt./226

(58) Field of Classification Search
USPC ..... Plt./263.1, 226
See application file for complete search history.

*Primary Examiner* — Kent L Bell
(74) *Attorney, Agent, or Firm* — Penny G. Aguirre

(57) ABSTRACT

A new cultivar of an interspecific hybrid of *Alyogyne* named 'HUTWOW' characterized by its well-branched stems, its finely divided foliage with short internode lengths, its large, open flowers that are lavender in color with a small burgundy colored eye and its continuous blooming habit when grown as a pot plant indoors and when grown in the landscape in climates with mild winters.

2 Drawing Sheets

Botanical classification: *Alyogyne huegelii×hakeifolia*.
Variety denomination: 'HUTWOW'.

BACKGROUND OF THE INVENTION

The present invention relates to a new and distinct cultivar of *Alyogyne* plant, botanically an interspecific hybrid between *Alyogyne huegelii* and *Alyogyne hakeifolia* and known as *Alyogyne* 'HUTWOW' and will be referred to hereinafter by its cultivar name, 'HUTWOW'. The new cultivar of *Alyogyne* is a shrub grown for landscape use. The *Alyogyne* species used in this hybrid were previous botanically classified as Hibiscus and are closely related.

The Inventor has been crossing native plant species from Australia and New Zealand for 45 years with the goal of producing unique plants that could be adapted to European climates and commercial growing protocols. His objective is to obtain unique plants of *Alyogyne* with better branching, finer foliage, increased resistance to cold, and larger and more open flowers in unique colors.

The Inventor made a cross in 2004 between unnamed plants from his breeding program of *Alyogyne huegelii* and *Alyogyne hakeifolia* at his nursery in Hornchurch, Essex, United Kingdom. The new cultivar was selected in 2005 and grown further for trials.

Asexual reproduction of the new cultivar was first accomplished by stem cuttings in Hornchurch, Essex, United Kingdom in 2005 by the Inventor. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'HUTWOW' as a unique cultivar of *Alyogyne*.

1. 'HUTWOW' exhibits well-branched stems.
2. 'HUTWOW' exhibits finely divided foliage with short internode lengths.

3. 'HUTWOW' exhibits large, open flowers that are lavender in color with a small burgundy colored eye.
4. 'HUTWOW' blooms continuously when grown as a pot plant indoors and when grown in a landscape in climates with mild winters.

'HUTWOW' can be compared to its parent plants, the unnamed plants of *Alyogyne huegelii* and *Alyogyne hakeifolia*. *Alyogyne huegelii* differs from 'HUTWOW' in having leaves that are more oak-like in form with irregularly dentated margins and having stems that are poorly branched and brittle. *Alyogyne hakeifolia* differs from 'HUTWOW' in having flowers that are tubular in shape, less open and mauve in color and in having stems that are poorly branched. 'HUTWOW' can also be compared to the *Alyogyne huegelii* cultivar, 'Santa Cruz' (not patented) and *Alyogyne hakeifolia* cultivar 'Melissa Anne' (not patented). 'Santa Cruz' differs from 'HUTWOW' in having light purple flowers with yellow anthers and white stigmas and in having larger leaves. 'Melissa Anne' differs from 'HUTWOW' in having flowers that are deep pink in color.

BRIEF DESCRIPTION OF THE DRAWING

The accompanying colored photographs illustrate the overall appearance and distinct characteristics of the new *Alyogyne*. The photographs were taken of a six month-old plant of 'HUTWOW' as grown in a 5-liter container in Hornchurch, Essex, United Kingdom.

The photograph in FIG. 1 shows the overall growth and flowering habit of 'HUTWOW'.

Figure 1:
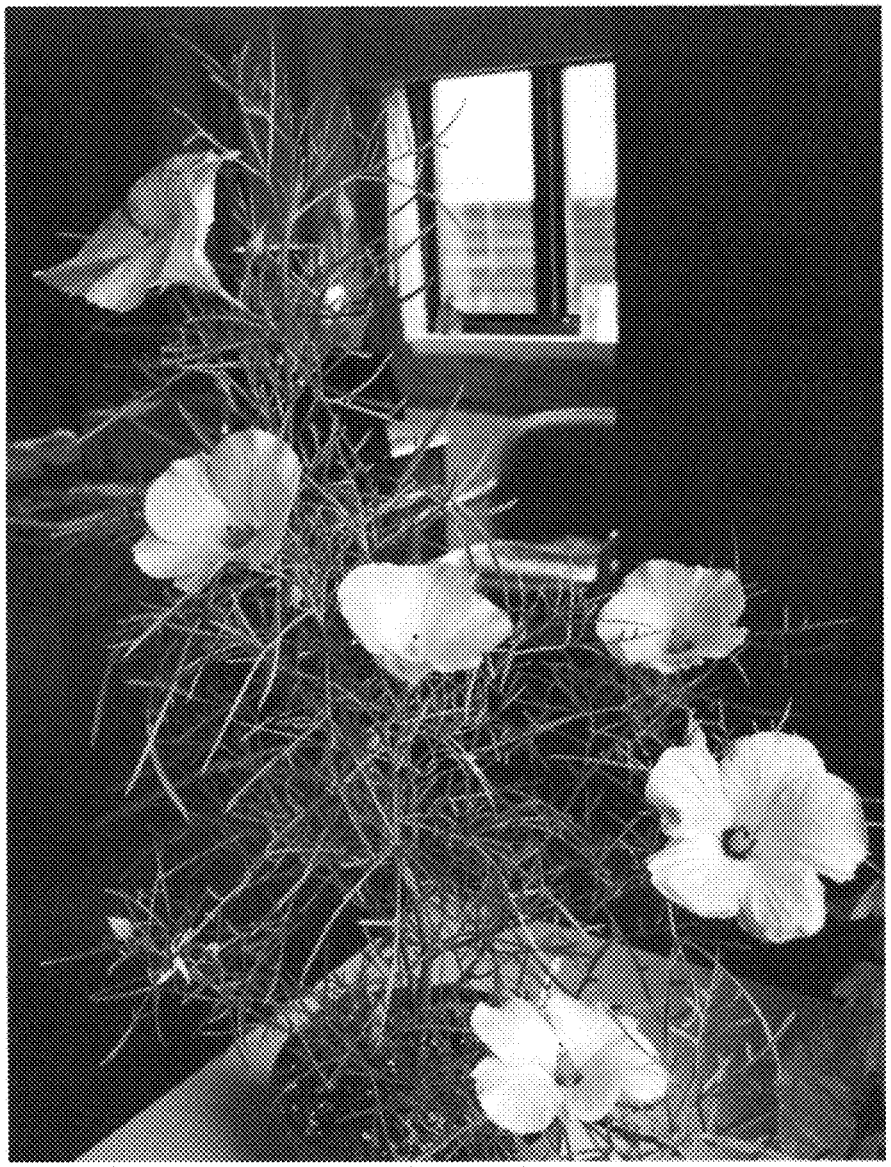
Figure 2:
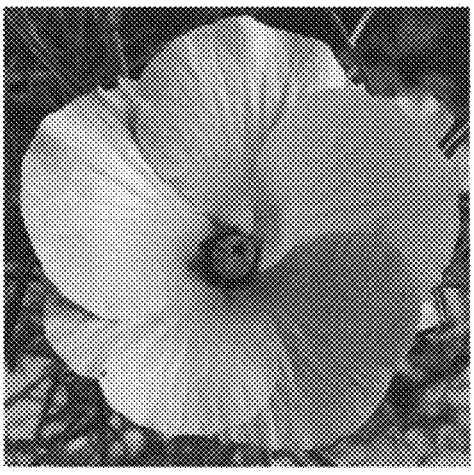

The photograph in FIG. 2 provides a close-up view of a young flower of 'HUTWOW'.

Figure 3:
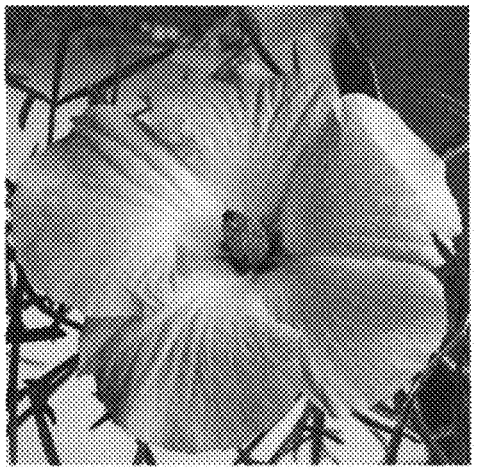

The photograph in FIG. 3 provides a close-up view of an older flower of 'HUTWOW'.

Figure 4:
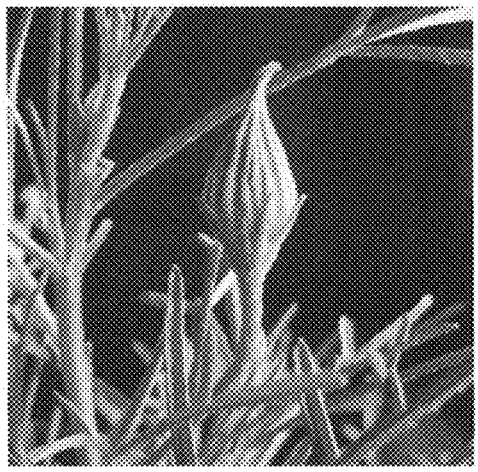

The photograph in FIG. 4 provides a close-up view of a flower bud of 'HUTWOW'.

Figure 5:
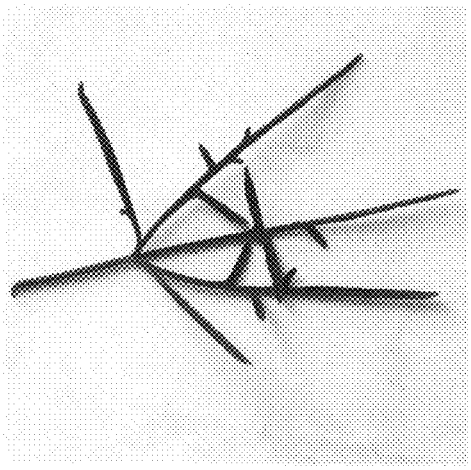

The photograph in FIG. 5 provides a close-up view of a leaf of 'HUTWOW'. The colors in the photograph may differ slightly from the color values cited in the detailed botanical description, which accurately describe the colors of the new *Alyogyne*.

DETAILED BOTANICAL DESCRIPTION

The following is a detailed description of the new cultivar as observed on six month-old plants of 'HUTWOW' as grown in 5-liter containers in Hornchurch, Essex, United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms year around in mild climates and when grown indoors and blooms from early winter to early summer when grown in the landscape outdoors in southwestern U.S.A.

*Plant type*.—Evergreen in southwestern U.S.A.

*Plant habit*.—Well-branched, bushy, rounded in the landscape.

*Height and spread*.—Reaches up to 1.8 m in height about 1.5 m in spread in three years in the landscape.

*Cold hardiness*.—At least in U.S.D.A Zone 10.

*Diseases and pests*.—Relatively disease resistant with no particular resistance to specific diseases observed. Plant of the species *Alyogyne* can be subject to problems with scale insects or aphids, however no insect problems under the conditions grown in the United Kingdom or Southwestern U.S.A. have been observed.

*Root description*.—Fibrous.

Growth and propagation:

*Propagation*.—Stem cuttings.

*Growth rate*.—Vigorous in Southwestern U.S.A, more vigorous than is typical of plants of the family *Malvaceae*.

Stem description:

*Shape*.—Round.

*Stem color*.—137C.

*Stem size*.—An average of 4 mm in diameter and up to 1 m in length (in a 5-liter container).

*Stem surface*.—Pubescent, covered with occasional translucent stellate hairs.

*Branching habit*.—Freely branching from near base, stem held at 45° angle at emergence.

*Internode*.—An average of 4 cm in length.

Foliage description:

*Leaf division*.—Simple.

*Leaf margins*.—Palmatisect with 5 linear dissections, the dissections have pinnate linear dissections.

*Leaf size*.—Variable, an average of 11 cm in length and 12 cm in width.

*Leaf shape*.—Rounded overall with linear dissections.

*Leaf base*.—Lower divisions truncate to petiole.

*Leaf apex*.—Apex of dissections acute.

*Leaf venation*.—Palmate, 137B on upper surface and 137A on lower surface.

*Leaf attachment*.—Petiolate.

*Leaf arrangement*.—Alternate.

*Leaf surface*.—Dull with translucent stellate hairs on upper surface and lower surface.

*Leaf color*.—137A on upper and lower surface.

*Petioles*.—4 to 5 cm in length and an average of 2 mm in width, 137A in color, surface is covered with translucent stellate hairs.

*Stipules*.—Vestigial, deciduous, <1 mm in length and width.

Flower description:

*Inflorescence type*.—Single, present at leaf axils.

*Lastingness of flowers*.—About 7 days, self cleaning.

*Flower size*.—Average of 9 cm in depth and 10 cm in diameter.

*Flower fragrance*.—None.

*Flower aspect*.—Facing upright to sidewise.

*Flower buds*.—An average of 2.5 cm in length, up to 1.8 cm in diameter, ovoid in shape and narrowing to a pointed apex, 137B in color with vertical lines of pubescence.

*Flower type*.—Widely open funnel with un-fused petals.

*Petals*.—5, an average of 6.5 cm in length and 4.5 cm in width, broadly spathulate in shape, margins entire and slightly wavy, apex rounded, base narrowing then truncate, surface glabrous on upper and lower surface, color when opening and fully open on upper and lower surface; a color between 85B and 92A with shades of 92C and 92D towards base, blotch of N79B and N79C near funnel center on upper surface, color when fading upper and lower surface; 91B shading to 155A above blotch, blotch N79C.

*Calyx form*.—Campanulate, an average of 1.8 cm in diameter and 2.2 cm in height.

*Sepals*.—5 (joined near base), lanceolate in spar, acuminate apex, entire margins, base fused, an average of 2.2 cm in length and 8 mm in width, 143C in color on upper and lower surface, surface is pubescence with translucent stellate hairs.

*Epicalyx*.—7 to 9 mm in length and about 9 mm in width, 10 sections with base fused, un-fused portion is linear in shape and 1 mm in width 143C in color.

*Peduncles*.—An average of 6.5 cm in length and 2 mm in diameter, round in shape, 138A in color, surface is covered with translucent hairs, one small leaf per peduncle in mid section; linear in shape, about 2 mm in length and <0.5 mm in width, 138A in color on both surfaces, surface covered with translucent hairs.

Reproductive organs:

*Gynoecium*.—5 pistils, about 9 mm in length, stigmas are about 3 mm in diameter and N187A in color, style are united into column about 2.6 cm in length and 1 mm in width and 155A with streaks of 187D in color, ovary is 7 mm in length and 8 mm in width, cylindrical and 5-angled in shape, superior, color 155A and 187D at apex and at angles.

*Androcoecium*.—Numerous and joined at base to form a stamina column (raceme-like) 2 cm in length and 3 mm in width surrounding the pistil, anthers are 1 mm in length, 0.5 mm in width, and 179B in color, filament is 2 mm in length and N74B in color, pollen is abundant and 169D in color.

*Fruit/seeds*.—Fruit; 5-celled, ovoid with flattened apex, 8 mm in length and 6 mm in width, 160D in color, seed; numerous, ovoid in shape, 159D in color, <1 mm in length and 1 mm in width.

It is claimed:

1. A new and distinct cultivar of *Alyogyne* plant named 'HUTWOW' as herein illustrated and described.

* * * * *